(12) United States Patent
Otsuka et al.

(10) Patent No.: US 10,915,617 B2
(45) Date of Patent: Feb. 9, 2021

(54) IMAGE PROCESSING APPARATUS, IMAGE PROCESSING METHOD, AND RECORDING MEDIUM

(71) Applicant: CASIO COMPUTER CO., LTD., Tokyo (JP)

(72) Inventors: Toshihiko Otsuka, Ome (JP); Takahiro Tomida, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 121 days.

(21) Appl. No.: 16/226,407

(22) Filed: Dec. 19, 2018

(65) Prior Publication Data
US 2019/0197223 A1 Jun. 27, 2019

(30) Foreign Application Priority Data

Dec. 22, 2017 (JP) ................................ 2017-246941
Oct. 24, 2018 (JP) ................................ 2018-200206

(51) Int. Cl.

| | |
|---|---|
| *G06F 21/32* | (2013.01) |
| *H04N 5/232* | (2006.01) |
| *A61B 5/021* | (2006.01) |
| *G06K 9/00* | (2006.01) |
| *A61B 5/00* | (2006.01) |
| *A61B 5/1171* | (2016.01) |
| *A61B 5/103* | (2006.01) |
| *G16H 20/00* | (2018.01) |

(52) U.S. Cl.
CPC ............ *G06F 21/32* (2013.01); *A61B 5/0077* (2013.01); *A61B 5/02108* (2013.01); *A61B 5/1032* (2013.01); *A61B 5/1176* (2013.01); *A61B 5/6891* (2013.01); *G06K 9/00288* (2013.01); *H04N 5/23222* (2013.01); *A61B 2576/02* (2013.01); *G16H 20/00* (2018.01)

(58) Field of Classification Search
CPC ... G06F 21/32; A61B 5/0077; A61B 5/02108; A61B 5/1032; A61B 5/1176; A61B 5/6891; A61B 2576/02; G06K 9/00288; H04N 5/23222; G16H 20/00
See application file for complete search history.

(56) References Cited

U.S. PATENT DOCUMENTS 9,854,976 B2   1/2018 Takamori et al.

FOREIGN PATENT DOCUMENTS

WO   2014136310 A1   9/2014

*Primary Examiner* — Mark Roz
(74) *Attorney, Agent, or Firm* — Holtz, Holtz & Volek PC

(57) ABSTRACT

An image processing apparatus includes an image analysis unit, a biometric information measurement unit, and a determination selection unit. The image analysis unit detects a plurality of part images of a subject from the image including the subject captured by the imaging unit. The biometric information measurement unit obtains biometric information from at least one of the plurality of part images of the subject detected by the image analysis unit.

The determination selection unit determines the detectability of biometric information on each of the plurality of part images of the subject detected by the image analysis unit. The determination selection unit makes a selection regarding acquisition of the biometric information of the subject on the basis of the detectability of the biometric information determined by the determination selection unit.

17 Claims, 9 Drawing Sheets

ALLOWING FREE STANDING BY PIVOTING OF
LEG UNIT ABOUT HINGE UNIT AS CENTER

IMAGE PROCESSING APPARATUS, IMAGE PROCESSING METHOD, AND RECORDING MEDIUM

CROSS-REFERENCE TO RELATED APPLICATIONS

The present application is based upon and claims the benefit of priority from Japanese Patent Application No. 2017-246941 filed on Dec. 22, 2017, and Japanese Patent Application No. 2018-200206 filed on Oct. 24, 2018, the content of which is incorporated herein in their entirety by reference.

BACKGROUND

This technical field relates to an image processing apparatus, an image processing method, and a recording medium.

In recent years, there is a technique for analyzing an image of a user to measure biometric information of the user.

For example, International Publication No. 2014/136310 discloses a configuration of detecting a predetermined part of a human body as a specific subject region from an image obtained by capturing a user so as to measure pulse wave velocity as one type of the biometric information.

Conventional techniques such as the technique disclosed in International Publication No. 2014/136310 causes deterioration in the measurement accuracy depending on an imaging state or the like.

SUMMARY

An image processing apparatus includes a processor, wherein the processor detects a plurality of part images of a subject from an image including the subject captured by an imaging unit, obtains biometric information from at least one of the plurality of detected part images of the subject, determines detectability of biometric information for each of the plurality of detected part images of the subject, and performs selection related to acquisition of the biometric information of the subject on the basis of the determined detectability of the biometric information.

An image processing method is executed by an image processing apparatus including a processor, the method including the steps of: detecting a plurality of part images of a subject from an image including the captured subject; obtaining biometric information from at least one of the plurality of detected part images of the subject; determining detectability of biometric information for each of the plurality of detected part images of the subject; and performing selection related to acquisition of the biometric information of the subject on the basis of the determined detectability of the biometric information.

There is provided a non-transitory computer-readable recording medium on which a computer readable program to be executed by an image processing apparatus including a processor is recorded, the program being provided to implement: a part detecting function of detecting a plurality of part images of a subject from an image including the captured subject; a biometric information acquisition function of obtaining biometric information from at least one of the plurality of detected part images of the subject; a determination function of determining detectability of biometric information for each of the plurality of detected part images of the subject; and a selection function of performing selection related to acquisition of the biometric information of the subject on the basis of the determined detectability of the biometric information.

A more detailed understanding of the present application can be obtained by consideration of the following detailed description together with the following drawings.

Figure 8:
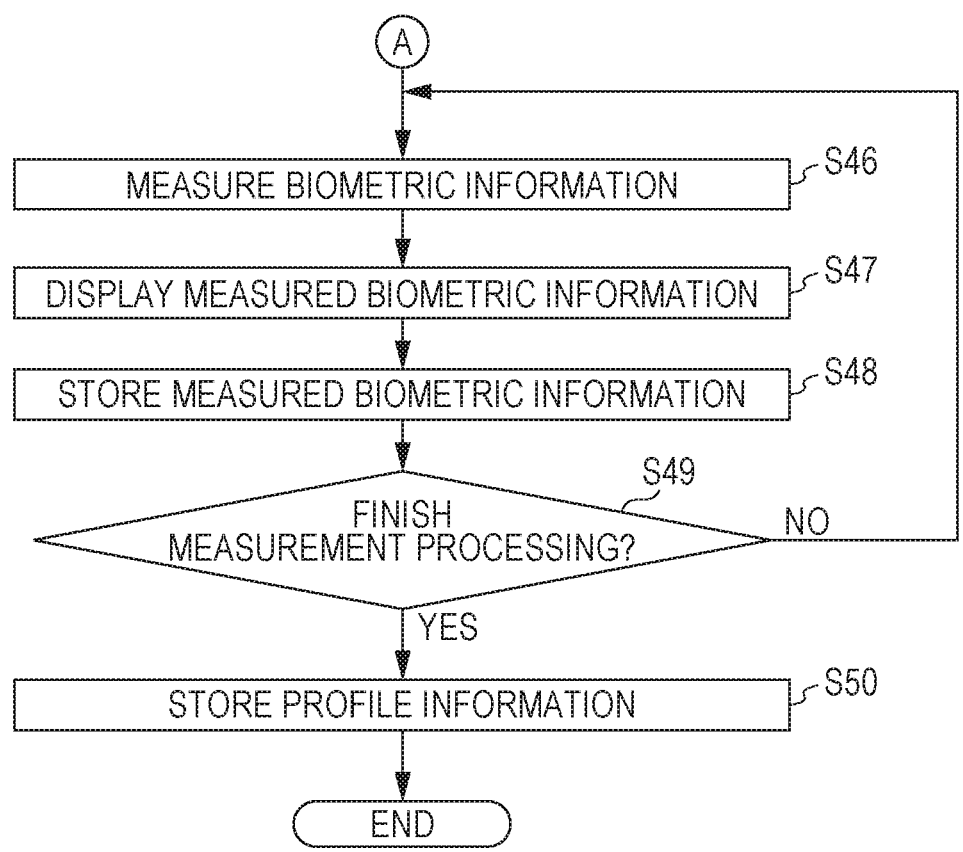
Figure 9:
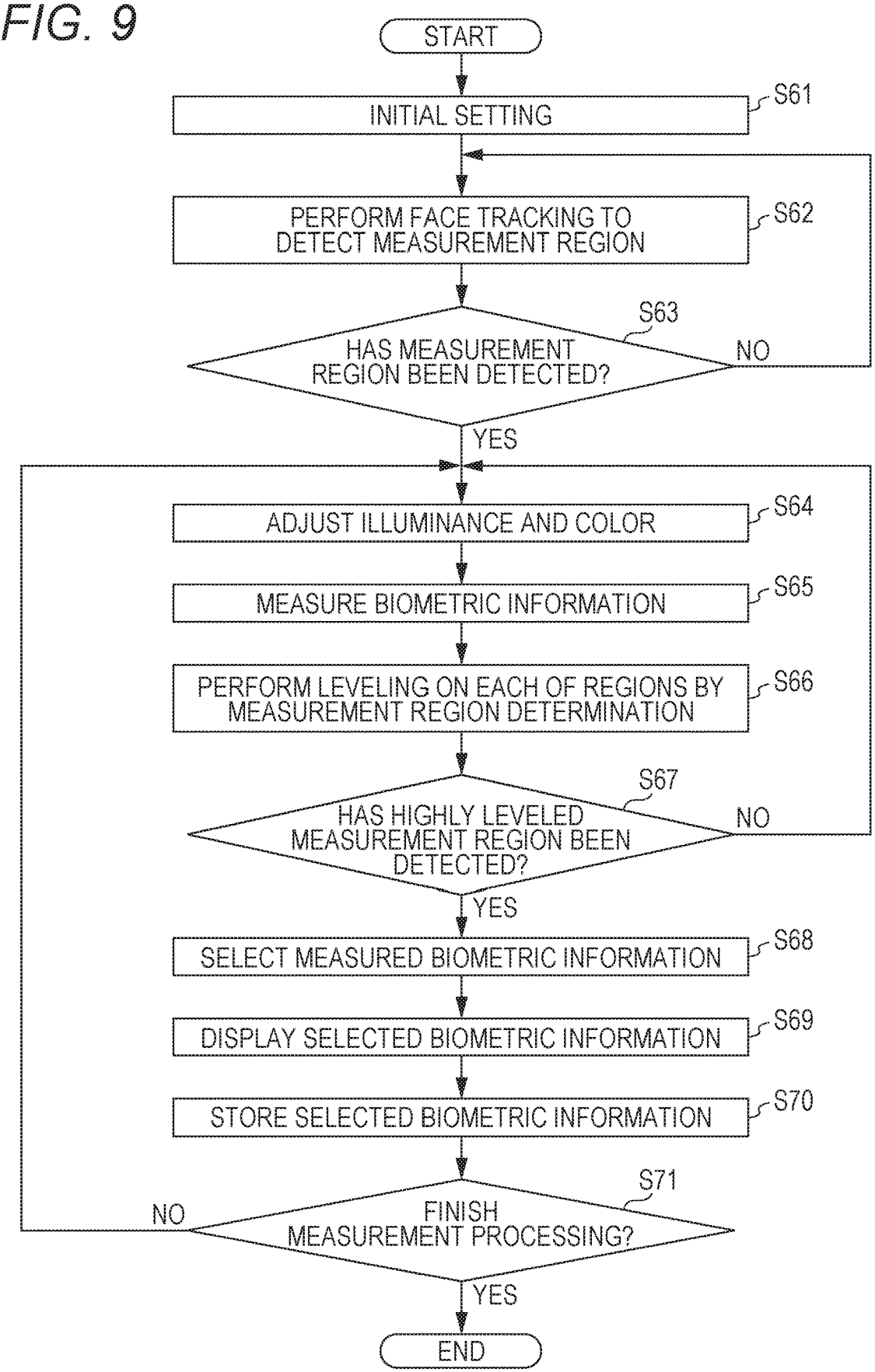

FIG. 8 is a flowchart (2/2) for explaining a flow of the second biometric information measurement processing executed by an image processing apparatus according to an embodiment of the present invention; and FIG. 9 is a flowchart illustrating a flow of first biometric information measurement processing executed by an image processing apparatus according to a modification of an embodiment of the present invention.

DETAILED DESCRIPTION

Hereinafter, embodiments of the present invention will be described with reference to the drawings.

An image processing apparatus 1 according to an embodiment of the present invention is configured as a user portable free-standing mirror. The image processing apparatus 1 determines availability of biometric information for each of a plurality of part images of the user. In addition, the image processing apparatus 1 selects a predetermined part image from the plurality of part images of the user on the basis of the determined availability of the biometric information (that is, detectability). Thereafter, the image processing apparatus 1 obtains the biometric information of the user from the selected predetermined part image.

According to this image processing apparatus 1, a part image for obtaining biometric information is selected on the basis of an index of availability of biometric information, making it possible to measure biometric information with higher accuracy.

[System Configuration]

Figure 1:
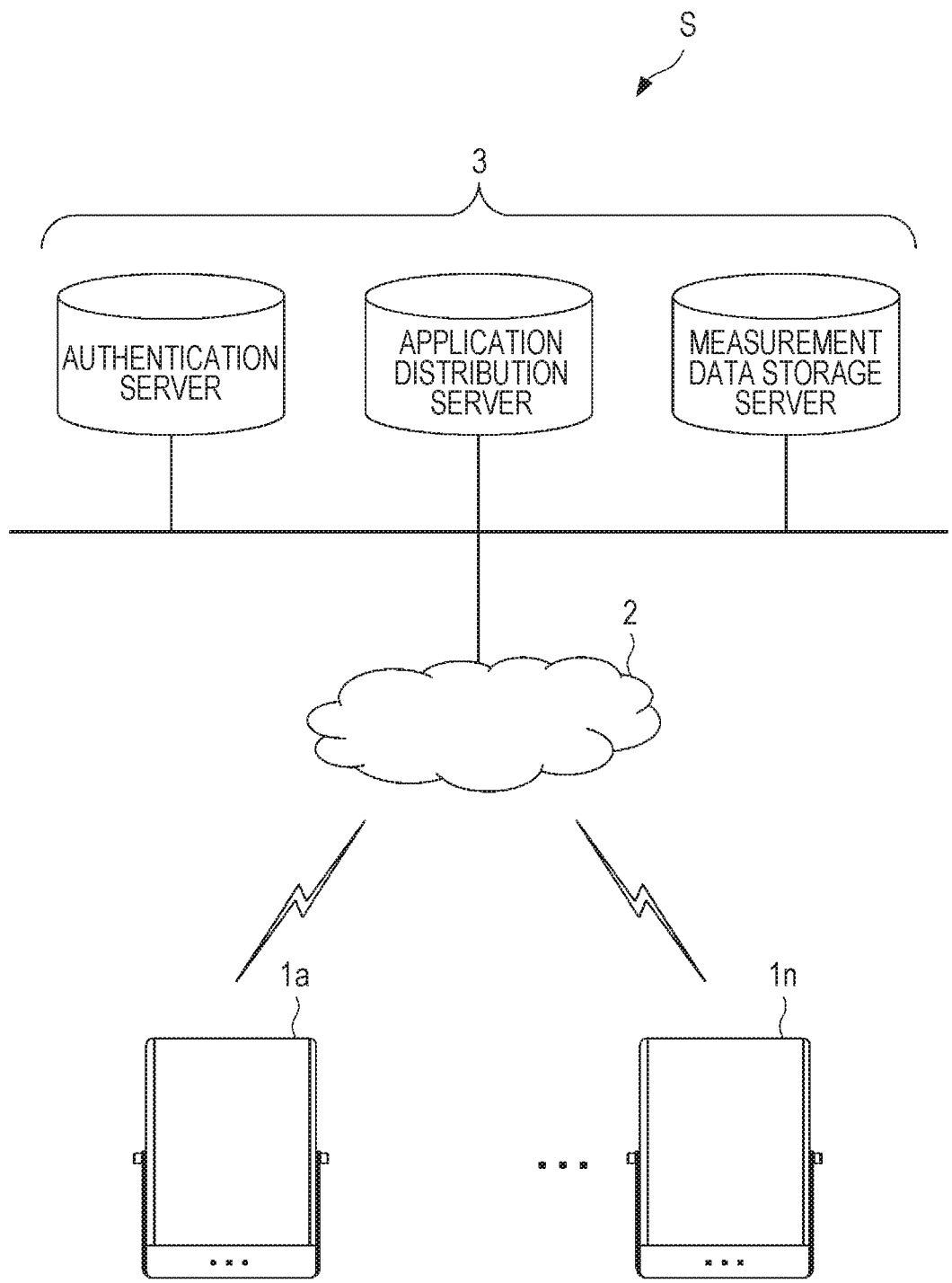
FIG. 1 is a block diagram illustrating a configuration of an image processing system according to an embodiment of the present invention.

FIG. 1 is a block diagram illustrating an overall configuration of an image processing system S including the image processing apparatus 1 according to the present embodiment. As illustrated in FIG. 1, the image processing system S includes a plurality of the image processing apparatuses 1, a network 2, and a server group 3.

There are no particular limitations on the number of the image processing apparatuses 1, and n image processing apparatuses 1 (n is an any natural number) may be included in the image processing system S. In the following description, in the case of describing n image processing apparatuses 1 without particularly distinguishing from each other, the alphabet at the end of the reference numeral is omitted, so as to be simply referred to as the "image processing apparatus 1".

As described above, the image processing apparatus 1 is an apparatus configure to select a part image used to obtain biometric information, on the basis of an index of availability of biometric information. The image processing apparatus 1 is communicably connected to each of servers included in the server group 3 via the network 2.

The network 2 is implemented by the Internet, a local area network (LAN), a mobile phone network, or a network combining these, for example.

The server group 3 includes various servers cooperating with the image processing apparatus 1. For example, the server group 3 includes an authentication server for authenticating the user of the image processing apparatus 1. Furthermore, for example, the server group 3 includes an application distribution server that distributes application software for implementing functions of the image processing apparatus 1. Furthermore, for example, the server group 3 includes a measurement data storage server that stores biometric information measured by the image processing apparatus 1 and user's profile information. Note that this is merely an example, and a server having other functions may be included in the server group 3. Furthermore, a plurality of servers included in the server group 3 may be implemented by separate server apparatuses individually, or may be implemented by a single server apparatus.

[External Configuration]

Figure 2:
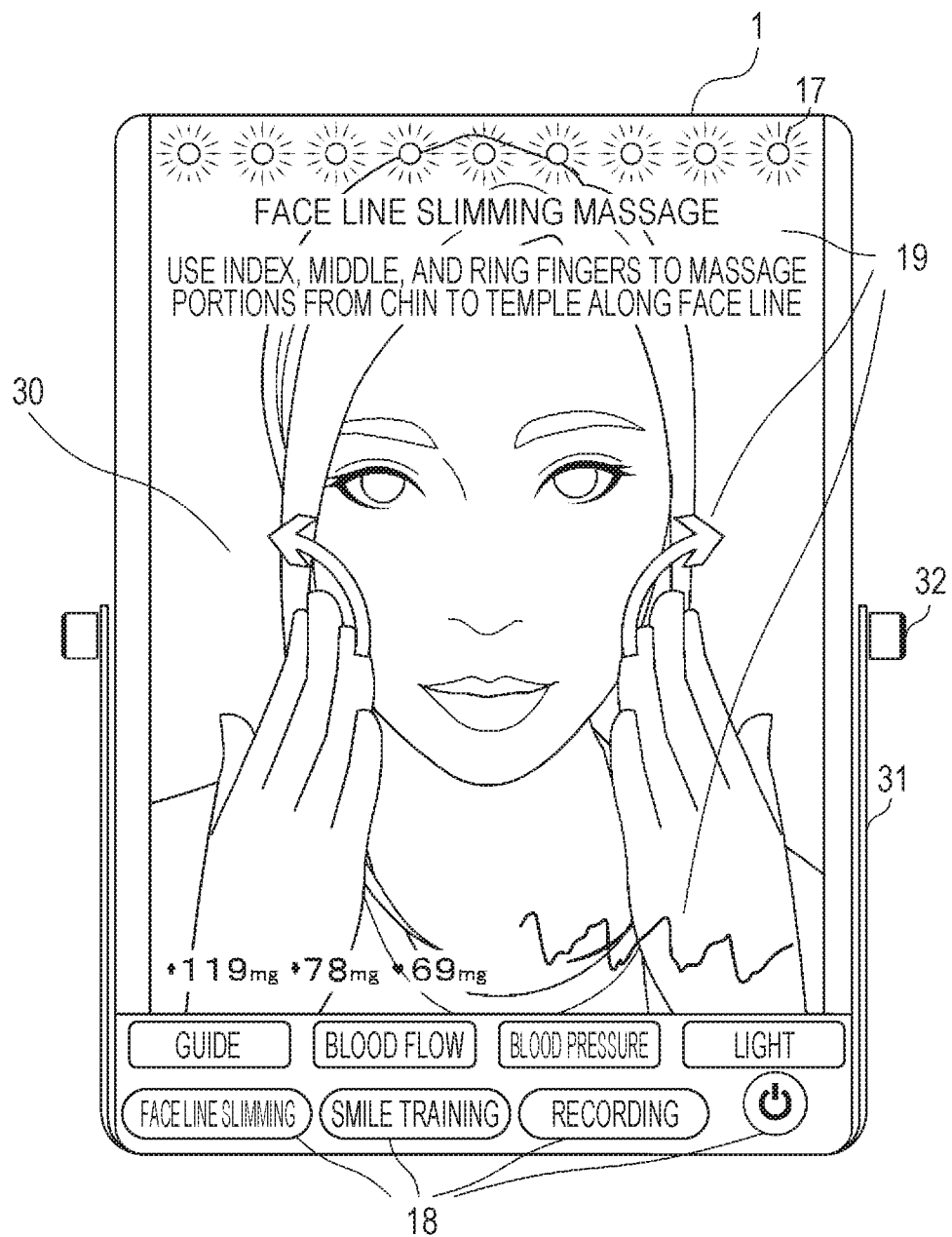
FIG. 2 is a configuration diagram illustrating an external configuration of a front surface of an image processing apparatus according to an embodiment of the present invention.
Figure 3A:
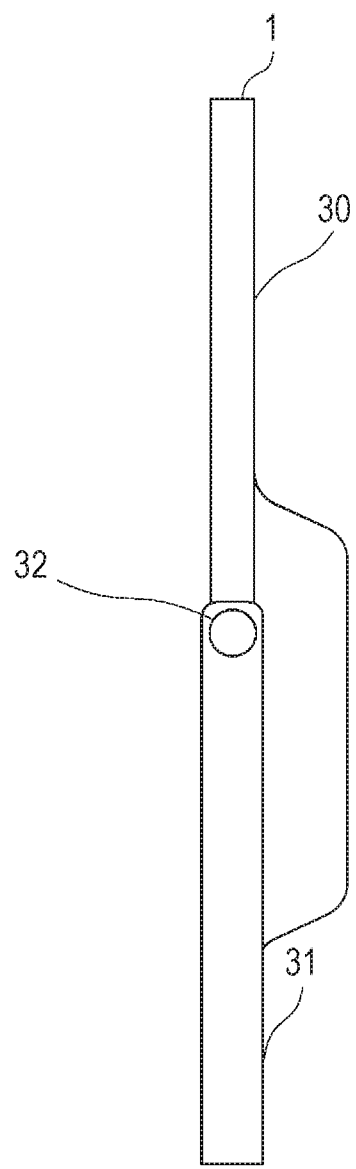
FIG. 3A is a configuration diagram illustrating an external configuration of a side surface of an image processing apparatus according to an embodiment of the present invention.
Figure 3B:
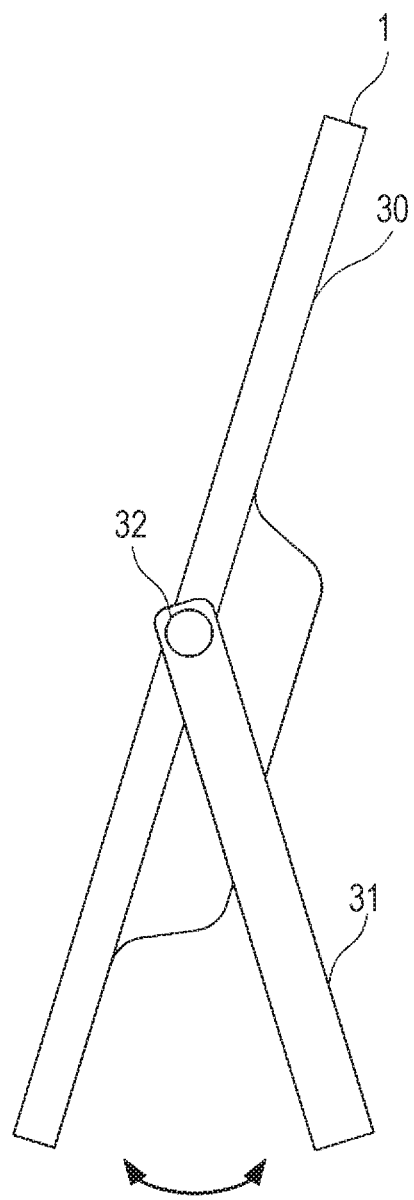
FIG. 3B is a configuration diagram illustrating an external configuration of a side surface of an image processing apparatus according to an embodiment of the present invention.

FIG. 2 is a configuration diagram illustrating an external configuration of a front surface of the image processing apparatus 1 according to an embodiment of the present invention. FIGS. 3A and 3B are configuration diagrams each illustrating an external configuration of a side surface of the image processing apparatus 1. The size of the front surface of the image processing apparatus 1 is formed to be A4 size defined by International Organization for Standardization (ISO) 216, for example.

As illustrated in FIGS. 2, 3A, and 3B, the image processing apparatus 1 includes a mirror unit 30 and a leg unit 31 and a hinge unit 32. The mirror unit 30 is a mirror having a reflecting surface.

The leg unit 31 and the hinge unit 32 are mechanisms enabling free-standing of the image processing apparatus 1.

The leg unit 31 is pivotably joined to the mirror unit 30 by the hinge unit 32.

As illustrated in FIG. 3A, the user can carry the image processing apparatus 1 with the side surface of the mirror unit 30 aligned with the side surface of the leg unit 31 so as to avoid becoming a bulky shape. In another case, as illustrated in FIG. 3B, where the user uses the image processing apparatus 1 installed on a desk or the like, the user pivots the leg unit 31 about the hinge unit 32 as a center point, enabling the image processing apparatus 1 to be free-standing. In order to enable the image processing apparatus 1 to be free-standing, the hinge unit 32 has a structure for holding the leg unit 31 in a state of maintaining a predetermined angle.

As illustrated in FIG. 2, the image processing apparatus 1 further includes a light emitting unit 17, an input unit 18, and a display unit 19 as a structure appearing on the external view.

The light emitting unit 17 is a portion that emits light to illuminate the user facing the mirror unit 30. The light emitting unit 17 illuminates the user to allow the image processing apparatus 1 to function as a mirror with illumination. In addition, the light emitting unit 17 performs light control in order to obtain biometric information in the biometric information measurement processing described below.

The light emitting unit 17 is arranged at a plurality of positions on an upper end of the mirror unit 30. For convenience of illustration, however, FIG. 2 attaches a reference numeral to one of the light emitting units 17 alone, and reference numerals for the other light emitting units 17 are omitted.

The input unit 18 is a portion that receives user's operation input. The input unit 18 is implemented by a plurality of buttons, for example. The figure illustrates, as an example, buttons for switching to various modes such as face line slimming, smile training, recording of biometric information, and buttons for power supply on/off for the image processing apparatus 1.

The display unit 19 is a portion that displays various types of information to notify the user of the various types of information. The display unit 19 displays, for example, messages such as texts, images, or the like. The image processing apparatus 1 arranges a reflecting surface of a reflecting section constituting the mirror unit 30 and a display surface of the display unit 19 to be superimposed with each other in a viewing direction of the user facing the mirror unit 30 so as to be simultaneously visible from the user.

For example, the display unit 19 constituted by a liquid crystal display is disposed on the deeper side in the viewing direction of the mirror unit 30 constituted by a two-way mirror, so as to be in parallel and overlapping with the mirror unit 30.

With this arrangement, the user can view one's own face reflected by the mirror unit 30 and the information displayed on the display unit 19 simultaneously. In the example of FIG. 2, a display region of the display unit 19 is provided at an upper portion of the screen, and a reflecting region of the mirror unit 30 is provided at a lower portion of the screen.

Although not illustrated in FIG. 2, the image processing apparatus 1 further includes an imaging unit 16. The imaging unit 16 is a portion that images a user facing the mirror unit 30 as a subject at the time of using the image processing apparatus 1. The imaging unit 16 is disposed at a position capable of capturing a face image of the user facing the mirror unit 30. For example, similarly to the display unit 19, the imaging unit 16 is arranged in parallel and overlapping with the display unit 19 on the deeper side in the viewing direction of the mirror unit 30 constituted by a two-way mirror.

The external structure of the image processing apparatus 1 has been described as above. However, this structure is merely an example, and the external structure of the image processing apparatus 1 is not limited to this example.

Furthermore, for example, the light emitting unit 17 may be disposed at the upper portion or the lower portion of the mirror unit 30, or may be disposed on the entire periphery of the mirror unit 30. Furthermore, for example, the number and arrangement of the input units 18 may be changed. Furthermore, for example, the display unit 19 may partially be configured as a touch panel, and the input unit 18 and the display unit 19 may be integrally configured.

Furthermore, for example, the display region implemented by the display unit 19 may be arranged at the upper portion of the screen, or may be arranged at another position. For example, on the assumption that the user's face is reflected in a central portion of the mirror unit 30, the display region may be arranged around the central portion.

Furthermore, for example, the mirror unit 30 may be arranged on a portion of the front surface of the image processing apparatus 1, and the display unit 19 may be arranged on another portion of the front surface. That is, the mirror unit 30 and the display unit 19 do not necessarily overlap with each other in the arrangement.

Furthermore, for example, it is allowable to constitute the mirror unit 30 with a normal mirror and constitute the display unit 19 with a transmission type liquid crystal display, instead of constituting the mirror unit 30 with a two-way mirror and constituting the display unit 19 with a normal liquid crystal display. In this case, it is preferable to set the mirror unit 30 constituted by a normal mirror to be arranged on a deeper side in the viewing direction of the display unit 19 constituted with a transmission type liquid crystal display so as to be in parallel and overlapping with the display unit 19.

[Hardware Configuration]

Figure 4:
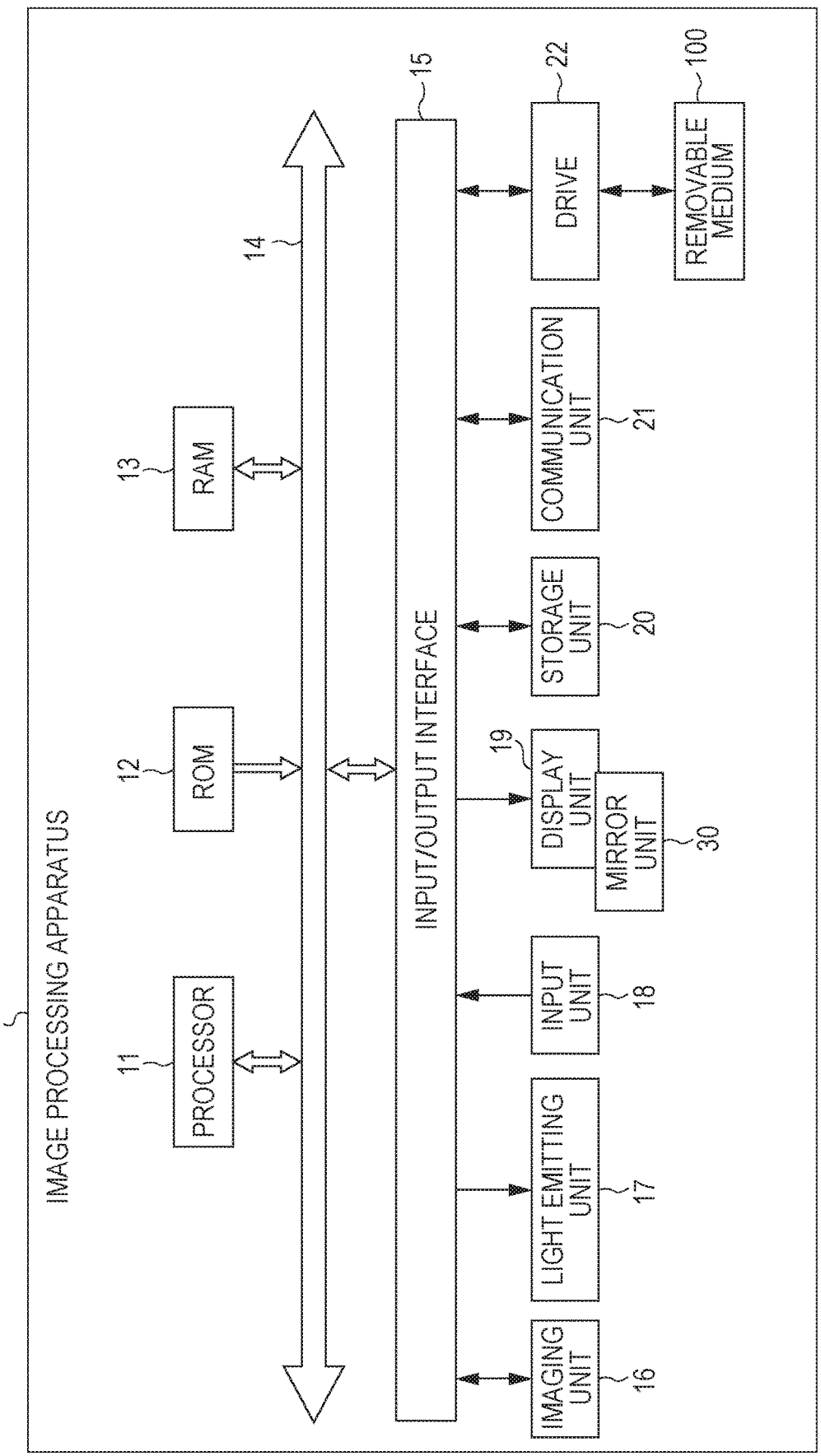
FIG. 4 is a block diagram illustrating a hardware configuration of an image processing apparatus according to an embodiment of the present invention.

FIG. 4 is a block diagram illustrating a hardware configuration of the image processing apparatus 1.

As illustrated in FIG. 4, the image processing apparatus 1 includes a processor 11, a read only memory (ROM) 12, a random access memory (RAM) 13, a bus 14, an input/output interface 15, the imaging unit 16, the light emitting unit 17, the input unit 18, the display unit 19, a storage unit 20, a communication unit 21, and a drive 22.

The processor 11 executes various types of processing in accordance with a program recorded in the ROM 12 or a program loaded from the storage unit 20 into the RAM 13.

The RAM 13 appropriately stores data or the like necessary for the processor 11 to execute various types of processing.

The processor 11, the ROM 12, and the RAM 13 are mutually connected via the bus 14. The bus 14 is also connected with the input/output interface 15. The input/output interface 15 is connected with the imaging unit 16, the light emitting unit 17, the input unit 18, the display unit 19, the storage unit 20, and the drive 22.

Although not illustrated, the imaging unit 16 includes an optical lens unit and an image sensor.

The optical lens unit includes a lens that collects light, for example, a focus lens, a zoom lens, etc., in order to photograph a subject.

The focus lens is a lens that forms a subject image on a light receiving surface of the image sensor.

The zoom lens is a lens that freely changes the focal length within a certain range.

The imaging unit 16 also includes a peripheral circuit for adjusting setting parameters such as focus, exposure, white balance, etc., as necessary.

The image sensor is constituted with a photoelectric conversion element, an analog front end (AFE), or the like.

The photoelectric conversion element is constituted with a complementary metal oxide semiconductor (CMOS) photoelectric conversion element, for example. A subject image is incident on the photoelectric conversion element from the optical lens unit. The photoelectric conversion element photoelectrically converts (images) the subject image, accumulates an image signal for a certain period of time, and sequentially supplies the accumulated image signal to the AFE as an analog signal.

The AFE executes various types of signal processing such as analog/digital (A/D) conversion processing on the analog image signal. A digital signal is generated by various types of signal processing so as to be output as an output signal of the imaging unit 16.

Such an output signal of the imaging unit 16 is appropriately supplied to the processor 11 or the like.

The light emitting unit 17 is constituted with: a light emitting body such as a light emitting diode (LED) corresponding to each of colors in the RGB color model; and a control circuit that controls the light emitting body. The control circuit controls the light emitting body to adjust the illuminance and the color component in the light emission of the light emitting body on the basis of the RGB color model. The light emitting unit 17 adjusts RGB color components to a predetermined state with the startup of the image processing apparatus 1 so as to illuminate the user. The predetermined state is a state in which the user's face displayed on the mirror unit 30 appears naturally. In addition, the light emitting unit 17 adjusts the illuminance and the color component to facilitate the measurement of the biometric information on the basis of the instruction from the processor 11 and emits light.

The input unit 18 includes various buttons, a microphone, or the like, and inputs various types of information in accordance with the user's instruction operation or user's instruction voice.

The display unit 19 is constituted with a liquid crystal display or the like and displays an image corresponding to the image data output by the processor 11. The mirror unit 30 is constituted with a two-way mirror, for example, to display the user's face. The arrangement of the display unit 19 and the mirror unit 30 is as described above with reference to FIG. 2.

The storage unit 20 is constituted with a semiconductor memory such as dynamic random access memory (DRAM) and stores various data.

The communication unit 21 performs communication control for the processor 11 to communicate with another device (for example, each of the servers included in the server group 3) via the network 2.

The drive 22 is constituted with an interface to which a removable medium 100 can be attached. The removable medium 100 in the form of a magnetic disk, an optical disk, a magneto-optical disk, a semiconductor memory, or the like is appropriately mounted on the drive 22. The removable medium 100 stores a program for executing biometric information measurement processing to be described below and various data such as image data. Programs and various data such as image data read out from the removable medium 100 by the drive 22 are installed in the storage unit 20 as necessary.

Note that the image processing apparatus 1 may further include other hardware devices in addition to the above-described hardware. For example, the image processing apparatus 1 may include an output unit formed with a lamp, a speaker, a vibration motor, or the like for outputting light, sound, or a vibration signal.

[Functional Configuration]

Figure 5:
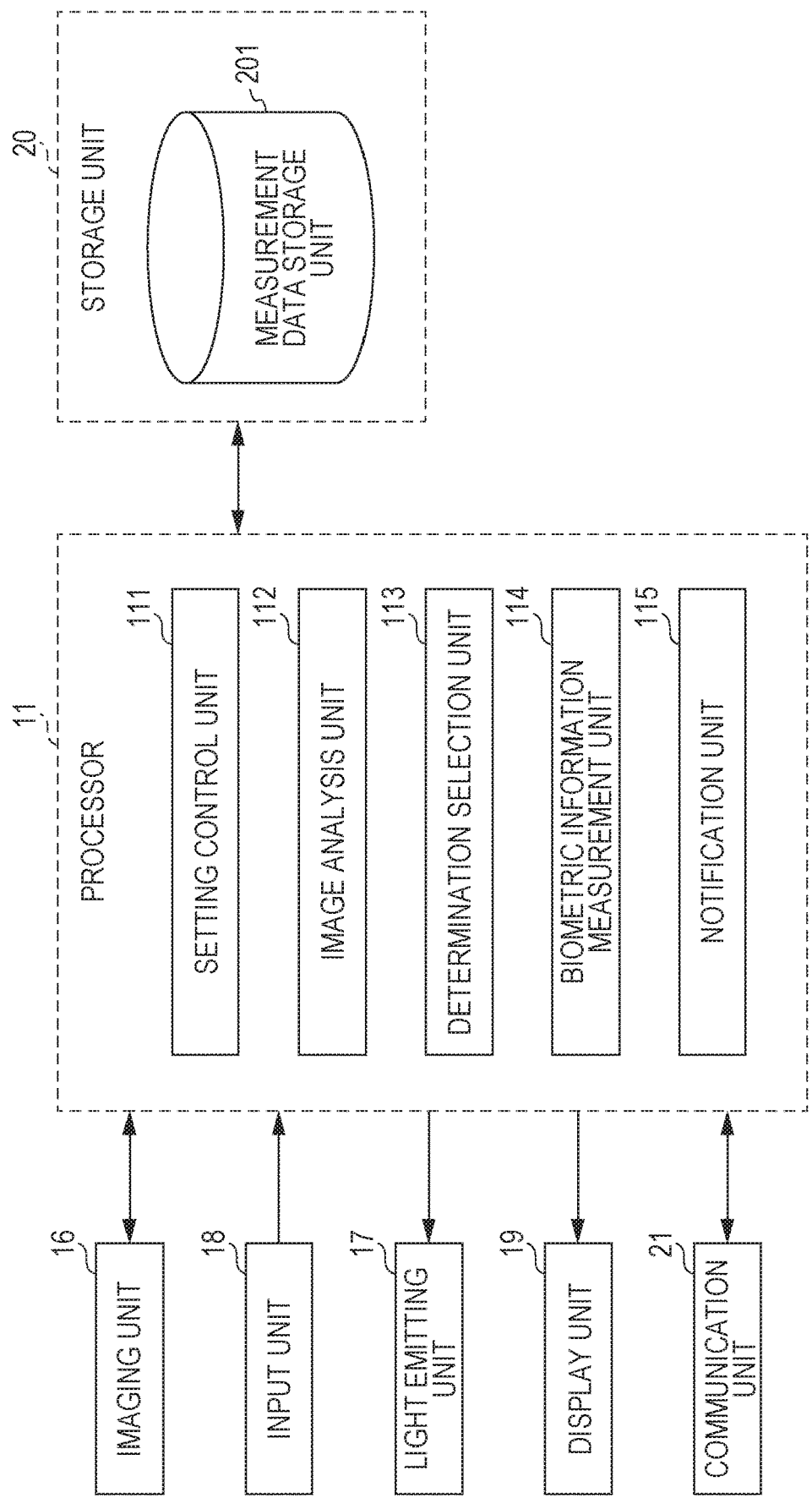
FIG. 5 is a functional block diagram illustrating a functional configuration for executing biometric information measurement processing among functional configurations of an image processing apparatus according to an embodiment of the present invention.

FIG. 5 is a functional block diagram illustrating a functional configuration for executing biometric information measurement processing among functional configurations of the image processing apparatus 1.

The biometric information measurement processing is a series of processing in which the image processing apparatus 1 captures an image of a user as a subject and obtains biometric information of the user from the captured image.

In a case where the biometric information measurement processing is executed, as illustrated in FIG. 5, the processor 11 includes a setting control unit 111, an image analysis unit 112, a determination selection unit 113, a biometric information measurement unit 114, and a notification unit 115 as functional portions.

Furthermore, a measurement data storage unit 201 is set in one region of the storage unit 20.

The measurement data storage unit 201 stores various data related to the biometric information measurement processing. For example, the measurement data storage unit 201 stores biometric information measured in the biometric information measurement processing and profile information such as a measurement region set with regard to a user being a processing target of the biometric information measurement processing.

Each of pieces of information stored in the measurement data storage unit 201 may either be stored in the storage unit 20 alone, or be appropriately stored in the removable medium 100 by the drive 22. Furthermore, each of the pieces of information stored in the measurement data storage unit 201 may be appropriately stored in the measurement data included in the server group 3.

The setting control unit 111 is a unit that performs control such as settings related to the biometric information measurement processing. For example, the setting control unit 111 obtains application software for performing biometric information measurement processing from the application distribution server included in the server group 3, and operates the application software. Furthermore, the setting control unit 111 communicates with the authentication server included in the server group 3, for example, so as to authenticate the user who performs the biometric information measurement processing. The setting control unit 111 further communicates with the measurement data storage server included in the server group 3, for example, so as to update the biometric information measured in the biometric information measurement processing and profile information of the measurement region or the like, set related to the user who is the processing target of the biometric information measurement processing.

The image analysis unit 112 analyzes an image including the user as a subject captured by the imaging unit 16 to detect a plurality of part images of the user included in the image. For example, the image analysis unit 112 performs processing related to face tracking such as pattern matching of contours and parts, skin color identification, or the like on a face image including the user's face so as to recognize the contour of the face, the positions of the eyes, and the skin region, leading to detection of measurement regions such as forehead, cheek, chin, and neck. Furthermore, the image analysis unit 112 notifies the determination selection unit 113 of the detected measurement region.

Note that the measurement region detected by the image analysis unit 112 corresponds to a region of interest (ROI) for noncontact acquisition of biometric information.

The determination selection unit 113 performs classification regarding availability of biometric information with respect to the measurement region detected by the image analysis unit 112. For example, the determination selection unit 113 performs leveling on each of the measurement regions in accordance with the availability of biometric information.

Leveling can be performed in any manner. For example, it is considered that the larger the measurement region, the more stable the measurement region is. Accordingly, the determination selection unit 113 performs leveling such that the larger the measurement region, the higher the level of the measurement region.

Alternatively, leveling is performed on the basis of the measurement result obtained by the biometric information measurement unit 114. For example, the determination selection unit 113 performs leveling on the basis of a pulse wave detection rate (probability of successful detection of the pulse wave) calculated on the basis of the pulse wave detected by the biometric information measurement unit 114. In this case, it is considered that the higher the pulse wave detection rate being the probability of successful detection of the pulse wave by the biometric information measurement unit 114, the more stable the measurement region is. Accordingly, the determination selection unit 113 performs leveling such that the higher the pulse measurement rate, the higher the level.

In addition, the determination selection unit 113 may control the light emitting unit 17 to adjust the illuminance and the color components so as to facilitate measurement of the biometric information.

The determination selection unit 113 that has performed the leveling in this manner selects a highly leveled region among the plurality of measurement regions detected by the image analysis unit 112 and notifies the biometric information measurement unit 114 of the selected measurement region.

The biometric information measurement unit 114 performs biometric information (also referred to as vital data in some cases) measurement directed to the image of the measurement region given in notification from the determination selection unit 113, without actually touching the user, that is, by user noncontact measurement. The measurement can be performed, for example, by analyzing the components in the vicinity of the heartbeat frequency on the basis of a green signal absorbed by subcutaneous blood hemoglobin in the measurement region. Examples of the biometric information measured by the biometric information measurement unit 114 are a pulse, a pulse wave, a blood flow, or the like.

In addition, the biometric information measurement unit 114 may perform measurement either on an image of one measurement region or on images of a plurality of measurement regions. In this case, the determination selection unit 113 selects a plurality of highly leveled measurement regions. The biometric information measurement unit 114 subsequently performs measurement on the plurality of measurement regions as targets. In this case, the biometric information measurement unit 114 performs measurement on the measurement regions of two distant points (for example, cheek and forehead, forehead-or-cheek and palm, etc.) at which the pulse delay is known, making it possible to measure the pulse wave velocity and the blood pressure fluctuation correlated with the pulse wave velocity.

In addition, the biometric information measurement unit 114 may perform noise removal or the like on the measured biometric information to perform averaging processing.

Measurement of biometric information by the biometric information measurement unit 114 can be performed by using the technique described in the following reference, for example.

<Reference>

Tohoku University Cyberscience Center Advanced Information Technology Research Division, Tohoku University Innovation Research Organization, "Successful in Developing" Blood Status Monitoring Device "The Mirror Magical" [online], Sep. 27, 2016 [Searched on Dec. 15, 2017], Internet <URL: http://www.tohoku.ac.jp/japanese/newimg/pressimg/tohokuuniv-press20160927_01web.pdf>

The biometric information measurement unit 114 notifies the notification unit 115 and the setting control unit 111 of the measured biometric information.

The notification unit 115 generates images for making notification of biometric information, such as graphs, numerical values, and icons, on the basis of the biometric information measured by the biometric information measurement unit 114. Thereafter, the notification unit 115 displays the generated image on the display unit 19 to perform notification. In this case, the notification unit 115 preferably performs notification in consideration of the position of the user's face on the mirror unit 30. The position of the user's face on the mirror unit 30 can be specified on the basis of the correspondence relationship between the reflection position on the mirror unit 30 and the display position on the display unit 19, and contour position of the user's face specified by face tracking performed by the image analysis unit 112.

For example, the notification unit 115 preferably automatically arranges and displays waveform data, necessary texts, or image information for making notification of biometric information in a region not overlapping with the position on which the user's face is reflected (that is, in the region not overlapping with the user's face). Redesigning and displaying such information in real time by the notification unit 115 would make it possible to easily convey information related to health condition, preventive instruction, or the like.

Alternatively, the notification unit 115 may display information to be superimposed at a position where the user's face is reflected, for example. For example, in order to obtain biometric information more easily, guide information may be displayed using an arrow or balloon to allow the user's face to directly face the mirror unit 30. For example, in order to keep the measurement region stable, it is possible to display a guide (using an arrow or computer graphics (CG) composite image) to arrange the face position (up, down, right, and left) to be directed to the front (position maximizing the contour region) from the contour data of face tracking to give an explicit feedback to the user, making it possible to obtain a stable measurement region continuously.

Furthermore, the notification unit 115 may combine these displays. For example, as illustrated in FIG. 2, the notification unit 115 may display text indicating specifics of massage in a region not overlapping with the position where the user's face is reflected, while displaying information with an arrow indicating hand movement in massage to be superimposed at a position where the user's face is reflected.

Furthermore, the notification unit 115 may perform notification by using a method other than display on the display unit 19. For example, the notification unit 115 may perform notification by outputting a voice message or the like from a speaker (not illustrated).

[Operation]

Next, operation of the image processing apparatus 1 will be described. Here, the image processing apparatus 1 performs first biometric information measurement processing and second biometric information measurement processing.

The first biometric information measurement processing is processing of leveling all detected measurement regions and then performing measurement of biometric information directed to a measurement region determined to be highly leveled. That is, the first biometric information measurement processing is processing of selecting and measuring a highly leveled location every time the processing is performed.

In contrast, the second biometric information measurement processing performs leveling for all detected measurement regions and then associates the measurement region determined to be highly leveled with each of users. Thereafter, biometric information measurement processing is performed directed to the measurement region associated. That is, the second biometric information measurement processing is processing of selecting a position set for each of users and performing measurement of the selected position.

Hereinafter, the first biometric information measurement processing will be described first with reference to FIG. 6. Next, the second biometric information measurement processing will be described with reference to FIGS. 7 and 8. Note that each of biometric information measurement processing is started together with startup of the image processing apparatus 1 or a user's starting operation. Examples of the user's starting operation are a user's instruction operation of starting biometric information measurement processing or user's instruction operation of switching to various modes such as face line slimming, smile training, recording of biometric information, or the like.

In this case, which biometric information measurement processing is to be performed is determined in accordance with the setting by the setting control unit 111 and user's selection operation.

[First Biometric Information Measurement Processing]

Figure 6:
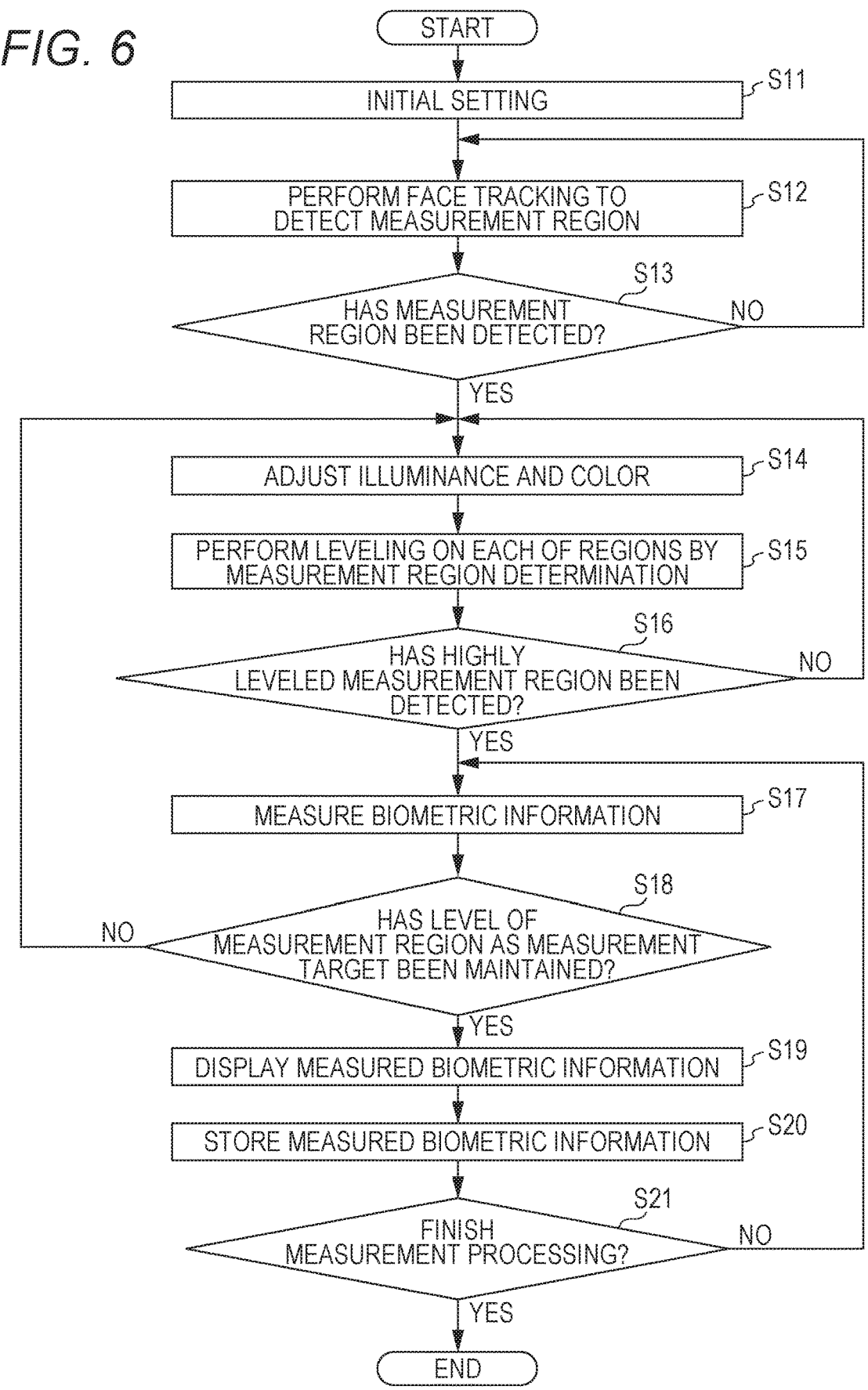
FIG. 6 is a flowchart for explaining a flow of first biometric information measurement processing executed by an image processing apparatus according to an embodiment of the present invention.

FIG. 6 is a flowchart for explaining a flow of the first biometric information measurement processing executed by the image processing apparatus 1.

In step S11, the setting control unit 111 performs initial setting. For example, the setting control unit 111 obtains application software for performing biometric information measurement processing from the application distribution server included in the server group 3, and operates the application software. In addition, the setting control unit 111 sets the imaging unit 16 and the light emitting unit 17 together with the operation of the application software. The setting control unit 111 causes the imaging unit 16 to start imaging and causes the light emitting unit 17 to start light emission.

In step S12, the image analysis unit 112 performs face tracking to detect a measurement region. Specifically, the image analysis unit 112 detects the user directly facing the mirror unit 30 and performs image analysis to further detect a measurement region. Examples of the measurement regions are regions corresponding to a forehead, a cheek, a chin, a neck, or the like.

In step S13, the image analysis unit 112 determines whether the measurement region has been successfully detected. In a case where the measurement region has been successfully detected, it is determined Yes in step S13, and the processing proceeds to step S14. In contrast, in a case where the measurement region has not been successfully detected because the orientation of the user's face is not appropriate, etc., the determination is No in step S13, and the processing returns to step S12. In step S13, the image analysis unit 112 may determine "Yes" on condition that at least one measurement region has been detected, or may determine "Yes" on condition that a predetermined number of measurement regions have been detected.

In step S14, the determination selection unit 113 controls the light emitting unit 17 to adjust the illuminance and the color components so as to facilitate measurement of the biometric information. In this case, in addition to the light emitting unit 17, the determination selection unit 113 may control the backlight of the display unit 19 to adjust illuminance and color components. Furthermore, the determination selection unit 113 may control, in addition to the light emitting unit 17, lighting equipment provided in the device other than the image processing apparatus 1 by using communication via the communication unit 21 so as to adjust the illuminance and the color component. This enables stable measurement suitable for the environment.

In step S15, the determination selection unit 113 performs leveling on each of the measurement regions detected in step S12. As described above, the leveling method is performed in accordance with the size of each of the measurement regions and the pulse wave detection rate of each of the measurement regions. In a case where leveling is performed on the basis of the pulse wave detection rate, the biometric information measurement unit 114 performs measurement on each of the detected measurement regions, and then calculates a pulse wave detection rate for each of the detected measurement regions.

In step S16, the determination selection unit 113 determines whether a highly leveled measurement region (that is, a measurement region with a level at a predetermined level or more) has been detected in the leveling performed in step S15.

In a case where a highly leveled measurement region has been detected, it is determined Yes in step S16, and the processing proceeds to step S17. In contrast, in a case where a highly leveled measurement region has not been detected, it is determined No in step S16, and the processing returns to step S14.

In step S17, the biometric information measurement unit 114 measures biometric information from the highly leveled measurement region. As described above, this measurement is performed on the basis of the image of the measurement region, and thus, is user noncontact measurement.

In step S18, the determination selection unit 113 performs leveling again on the measurement region that is defined as a target of actual measurement of the biometric information in step S17. Then, it is determined whether this measurement region remains highly leveled. In a case where the measurement region remains highly leveled, it is determined Yes in step S18, and the processing proceeds to step S19.

In contrast, in a case where the level of this measurement region has changed and is not highly leveled any more, then a determination of step S18 is No and the processing returns to step S14. For example, in a case where it takes several seconds to several tens of seconds to measure the biometric information in step S17, the user might change the orientation of the face or the like during measurement. In this case, the measurement region might not be appropriately imaged leading to degrading the level of the measurement region. In this case, it is determined No in step S18.

With execution of reconfirmation of the level after measuring the biometric information in the processing of step S18, it is possible in the present embodiment to obtain biometric information measured directed to highly leveled measurement region alone (that is, selectively directed to the measurement region that can be measured with high accuracy). Note that this re-leveling may be performed on the basis of conditions other than the end of biometric information measurement. For example, this re-leveling may be performed on condition that a predetermined time (for example, 30 minutes) has elapsed from the previous leveling in step S15. That is, this re-leveling may be executed on a regular basis. In addition to this, for example, this re-leveling may be performed on condition that a user's operation instruction has been received.

In step S19, the notification unit 115 makes notification of the biometric information measured in step S17 by using a method of displaying the information on the display unit 19, for example.

In step S20, the setting control unit 111 stores the biometric information measured in step S17 in the measurement data storage unit 201 of the storage unit 20, the measurement data storage server or the like included in the server group 3. By associating the stored measurement data with the user as a measurement target, it is possible to generate a history of the biometric information of the user. This history can be used for the purpose of analyzing the transition of the user's biometric information, for example. In addition, even in a case where measured data is not associated with a user being a measurement target, the data can still be used for statistical analysis or the like as "big data".

While the above describes that step S20 is executed after step S19 for convenience, step S19 may be executed after step S20, or step S19 and step S20 may be executed in parallel.

In step S21, the setting control unit 111 determines whether to finish the first biometric information measurement processing. For example, the setting control unit 111 determines whether to finish the first biometric information measurement processing on condition that: the biometric information has been measured a predetermined number of times; the processing end operation has been received from the user; or a predetermined time has elapsed from the start of the first biometric information measurement processing.

In a case where such a condition for finishing the first biometric information measurement processing is not satisfied, it is determined No in step S21, and the processing returns to step S17. In contrast, in a case where the condition for finishing the first biometric information measurement processing is satisfied, it is determined Yes in step S21, and the first biometric information measurement processing of this time is finished.

Note that in the first biometric information measurement processing performed in subsequent times, it is allowable to configure to omit the processing such as acquisition of the application in step S11.

With execution of the first biometric information measurement processing described above, it is possible to select a highly leveled measurement region from among the detected measurement regions and to perform measurement of biometric information directed to the selected measurement region. Here, since the highly leveled measurement region is a measurement region where biometric information is easy to measure, it is possible to measure biometric information with higher accuracy by using the first biometric information measurement processing.

In addition, the first biometric information measurement processing makes confirmation that the measurement region remains highly leveled with no degrading of level after measuring the biometric information, making it possible to ensure execution of biometric information measurement with higher accuracy.

Furthermore, the first biometric information measurement processing is capable of measuring biometric information even without preliminary registration of user profile information.

[Second Biometric Information Measurement Processing]

Figure 7:
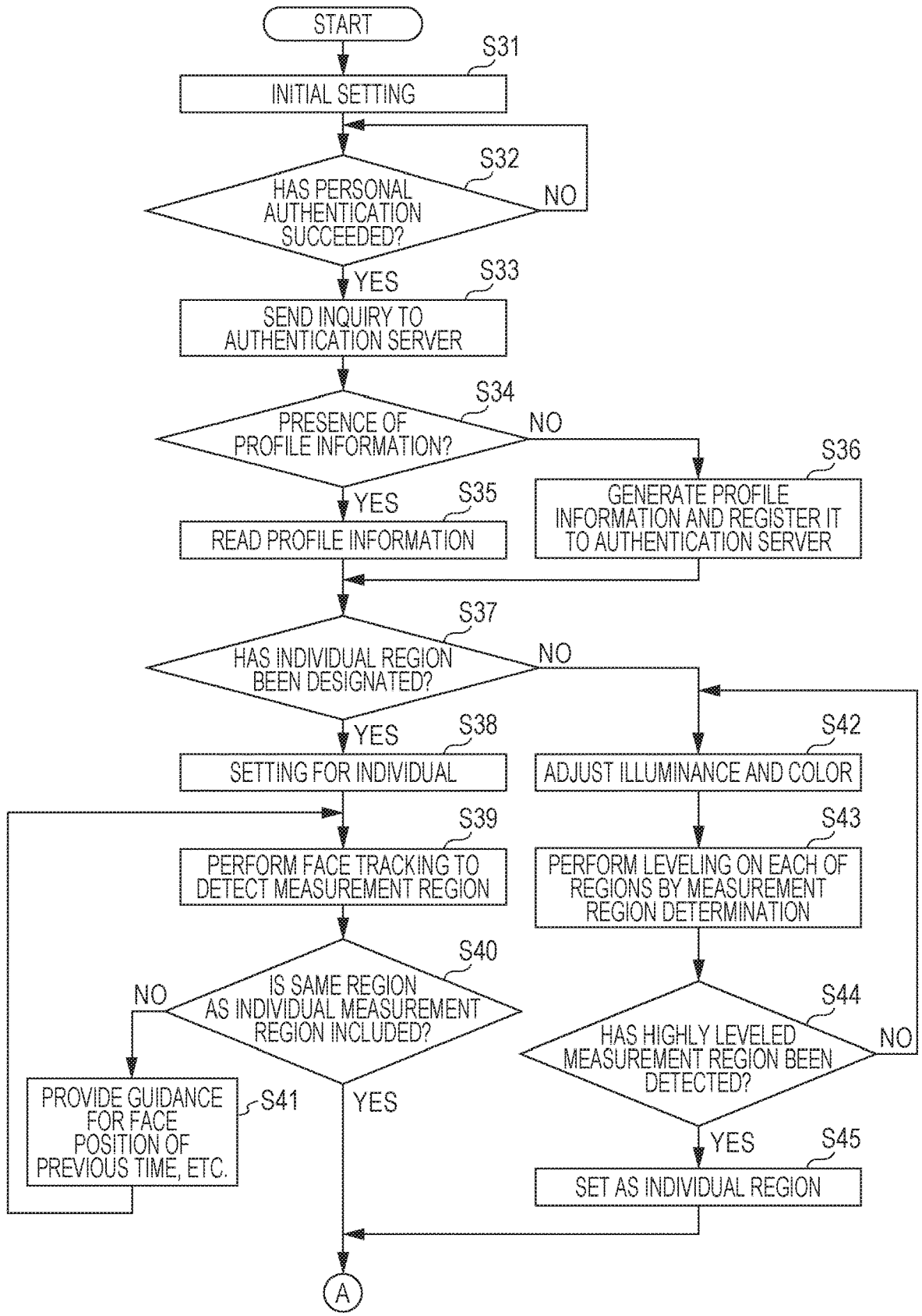
FIG. 7 is a flowchart (1/2) for explaining a flow of second biometric information measurement processing executed by an image processing apparatus according to an embodiment of the present invention.

FIGS. 7 and 8 are flowcharts for explaining a flow of the second biometric information measurement processing executed by the image processing apparatus 1.

In step S31, the setting control unit 111 performs initial setting. Since the initial setting method is similar to the above-described step S11, detailed description will be omitted.

In step S32, the setting control unit 111 attempts personal authentication for identifying the user, and determines whether the personal authentication is successful. In a case where the personal authentication is successful, it is determined Yes in step S32, and the processing proceeds to step S33. In a case where the personal authentication fails, it is determined No in step S32, and step S32 is repeated. Personal authentication may be implemented by face recognition using the face image of the user captured by the imaging unit 16, voice print recognition using the user's voice collected by the microphone included in the input unit 18, for example. In addition to this, personal authentication may be performed by other authentication methods such as biometric authentication using predetermined biometric information or authentication using a password input from the user.

In step S33, the setting control unit 111 inquires of the authentication server included in the server group 3 the profile information regarding the user specified by personal authentication. The authentication server confirms the presence or absence of profile information regarding the user as a target of inquiry. In a case where there is profile information, the authentication server obtains corresponding profile information from the measurement data storage server included in the server group 3. The authentication server transmits the obtained profile information to the setting control unit 111 as a response to the inquiry. Along with this, in a case where there is profile information, the authentication server transmits a notification to that effect to the setting control unit 111 as a response to the inquiry.

Here, the profile information includes related information of the user, the individual region designated for the user, and the type of biometric information as a measurement target designated for the user.

Here, examples of the related information of the user include identification information for identifying the user, information such as the user's name, age, height, and weight, and an authentication source image for performing authentication.

In addition, the individual region is a specific measurement region associated with each of the users. Furthermore, the number of individual regions varies depending on the biometric information as a measurement target. For example, as described above, measurement of pulses and pulse waves can be performed from one measurement region (for example, one measurement region such as forehead, cheek, chin, and neck). Therefore, it is sufficient to have one individual region in a case where pulses or pulse waves are to be measured. In contrast, measurement of the pulse wave velocity or blood pressure fluctuation can be performed at two distant measurement regions (for example, cheek and forehead, or, forehead-or-cheek and palm, etc.) at which the pulse delay is known. Therefore, two individual regions would be required in a case where pulse wave velocity or blood pressure fluctuation is to be measured.

Note that the profile information may further include related information related to measurement, such as specifics of the setting of the light emitting unit 17 at the time of measurement.

In step S34, the setting control unit 111 confirms specifics of the response from the authentication server. In a case where the specifics of the response from the authentication server are profile information, it is determined Yes in step S34, and the processing proceeds to step S35. Meanwhile, in a case where the specifics of the response from the authentication server indicate the absence of the profile information, determination is No in step S34, and the processing proceeds to step S36.

In step S35, the setting control unit 111 reads the profile information received as a response from the authentication server.

In step S36, the setting control unit 111 generates profile information regarding the user as a current processing target, transmits it to the authentication server, and requests registration of the profile information. The authentication server stores the received profile information in the measurement data storage server to perform registration. Note that in a case where the individual region setting has not been completed at this stage, information other than the individual region alone is registered.

In step S37, the setting control unit 111 determines whether an individual region has been designated for the user as the processing target.

For example, in a case where designation of the individual region is included in the profile information read in step S35, or where the individual region has been designated in response to user's operation or the like, determination is Yes in step S37 and the processing proceeds to step S38. In contrast, in a case where designation of the individual region is not included in the profile information, and where the individual region has not been designated in response to user's operation or the like, determination is No in step S37 and the processing proceeds to step S42.

In step S38, the setting control unit 111 performs setting according to the individual user on the basis of the profile information. For example, the setting control unit 111 sets the individual region, the type of the biometric information as a measurement target, the setting specifics of the light emitting unit 17 at the time of measurement, or the like, on the basis of the profile information. In other words, the setting control unit 111 performs setting to a state suitable for measurement on the user.

In step S39, the image analysis unit 112 performs face tracking to detect a measurement region. Since this processing is the same processing as the above-described step S12, detailed description will be omitted.

In step S40, the determination selection unit 113 determines whether the measurement region detected in step S39 includes the same region as the individual region set in step S38. Note that in a case where there is a single individual region alone, it is determined whether the same area is included in this single individual region. In a case where there are two individual regions, it is determined whether the same region is included in each of these two individual regions.

The same region as the individual region (in a case where there are two individual regions, the same region in each of the individual regions) is included, it is determined Yes in step S40 and the processing proceeds to step S46.

In contrast, in a case where the same region as the individual region (in the case of two individual regions, the same region for each of the individual regions) is not included, it is determined No in step S40, and the processing proceeds to step S41.

In step S41, the notification unit 115 makes notification of guidance (navigation) to detect the same region as the individual region so to achieve the face position at the previous measurement (that is, the position at which the individual region was detected), or the like. For example, the notification unit 115 uses an arrow or a balloon to display the guidance information so that the position and orientation of the user's face captured by the imaging unit 16 are the same as the position and orientation at the previous measurement. The user can refer to this guidance display to adjust the face position and orientation so as to be the same as the position and orientation at the previous measurement.

This enables in the next step S39 detection of the same measurement region as the individual region, leading to determination of Yes in the next step S40.

Meanwhile, in the case of proceeding to step S42, the processing for setting the individual region is started. Specifically, in step S42, the determination selection unit 113 controls the light emitting unit 17 to adjust the illuminance and the color components so as to facilitate measurement of the biometric information. Since this processing is the same processing as the above-described step S14, detailed description will be omitted.

In step S43, the determination selection unit 113 performs leveling on each of the measurement regions detected in step S32. Since this processing is the same as the above-described processing of step S15, detailed description will be omitted.

In step S44, the determination selection unit 113 determines whether a highly leveled measurement region (that is, a measurement region with a level at a predetermined level or more) has been detected in the leveling performed in step S43.

In a case where two individual regions are needed, it is determined whether a highly leveled measurement region has been detected at each of the different places. For example, it is determined whether a highly leveled measurement region has been detected, such as one position in the forehead and one position in the cheek.

In a case where a highly leveled measurement region has been detected (that is, a highly leveled measurement region is detected in each of different positions in a case where two individual regions are necessary), it is determined Yes in step S44, and the processing proceeds to step S45. On the other hand, when a highly leveled measurement region is not detected (when two individual regions are necessary, in a case where a highly leveled measurement region is not detected in each of different places), it is determined No in step S44, and the processing returns to step S42.

In step S45, the highly leveled measurement region (highly leveled measurement region for each of the different places when two individual regions are needed) detected in step S44 is set as an individual region of the user as a processing target of this time. Note that specifically which positions differ may be predetermined for each of the users or may be determined on the basis of where the highly leveled measurement region detected in step S44 is positioned.

In step S46, the biometric information is measured from the individual region detected in step S39 or the individual region set in step S45. As described above, this measurement is performed on the basis of the image of the measurement region, and thus, is user noncontact measurement.

In step S47, the notification unit 115 makes notification of the biometric information measured in step S46 by using a method of displaying the information on the display unit 19, for example. Since this processing is the same processing as the above-described step S19, detailed description will be omitted.

In step S48, the setting control unit 111 stores the biometric information measured in step S46 in the measurement data storage unit 201 of the storage unit 20, the measurement data storage server or the like included in the server group 3. Since this processing is the same processing as the above-described step S20, detailed description will be omitted.

In step S49, the setting control unit 111 determines whether to finish the second biometric information measurement processing. This processing is the same processing as the above-described step S21, and the condition for finishing the second biometric information measurement processing can also be set to the same condition as the condition for finishing the first biometric information measurement processing, and thus, detailed description will be omitted.

In a case where the condition for finishing the second biometric information measurement processing is not satisfied, it is determined No in step S49, and the processing returns to step S46. In contrast, in a case where the condition for finishing the second biometric information measurement processing is satisfied, it is determined Yes in step S49, and the processing proceeds to step S50.

In step S50, the setting control unit 111 updates the profile information on the basis of the content of the current processing and transmits the updated profile information to the authentication server, and requests the authentication server to register the profile information. For example, the setting control unit 111 updates the profile information on the basis of the individual region set in step S44 in this processing and the setting content of the light emitting unit 17 at the time of light control in step S42, or the like, and transmits the updated profile information to the authentication server, and requests the authentication server to register the profile information.

The authentication server stores the received profile information in the measurement data storage server to perform registration. This configuration enables determination of Yes in step S37 in the second biometric information measurement processing to be performed in subsequent times, making it possible to omit processing in steps S42 to S45 or the like.

Note that in the second biometric information measurement processing performed in subsequent times, it is allowable to configure to omit the processing such as acquisition of the application in step S31 as well.

In the second biometric information measurement processing described above, it is possible to perform measurement of biometric information directed to the individual region set for each of the users. Here, since the individual region is selected from the highly leveled measurement region, being a measurement region where biometric information is easy to measure, it is possible to measure biometric information with higher accuracy by using the second biometric information measurement processing.

Furthermore, according to the second biometric information measurement processing, setting is made such that the individual region is set for each of the users. Accordingly, even in a case where the highly leveled measurement region differs for each of individual users, it is possible to ensure that the biometric information is measured with higher accuracy.

The image processing apparatus 1 configured as described above includes the image analysis unit 112, the biometric information measurement unit 114, and the determination selection unit 113.

The image analysis unit 112 detects a plurality of part images of a subject from the image including the subject captured by the imaging unit 16.

The biometric information measurement unit 114 obtains biometric information from at least one of the plurality of part images of the subject detected by the image analysis unit 112.

The determination selection unit 113 determines the detectability of biometric information on each of the plurality of part images of the subject detected by the image analysis unit 112. The determination selection unit 113 makes a selection regarding acquisition of the biometric information of the subject on the basis of the detectability of the biometric information determined by the determination selection unit 113.

With this configuration of making selection regarding acquisition of biometric information on the basis of an index of detectability of biometric information, it is possible to measure the biometric information with higher accuracy.

The determination selection unit 113 selects a predetermined part image from the plurality of part images of the subject on the basis of the detectability of the biometric information determined by the determination selection unit 113.

The biometric information measurement unit 114 obtains the biometric information of the subject from the predetermined part image selected by the determination selection unit 113.

A part image used for obtaining biometric information is selected on the basis of an index of detectability of biometric information, making it possible to measure biometric information from a part image from which biometric information is obtained with higher availability.

The biometric information measurement unit 114 obtains biometric information from each of the plurality of part images of the subject detected by the image analysis unit 112.

The determination selection unit 113 selects biometric information from the plurality of pieces of biometric information obtained by the biometric information measurement unit 114 on the basis of the detectability of the biometric information determined by the determination selection unit 113.

This makes it possible to obtain biometric information measured from a part image from which biometric information is obtained with higher availability, on the basis of the index of detectability of biometric information.

The biometric information measurement unit 114 sets the acquisition method of the biometric information to vary in accordance with the detectability of the biometric information of the predetermined part image selected by the determination selection unit 113.

This makes it possible to measure the biometric information with high accuracy even when, for example, the setting is such that the higher the detectability of biometric information, the shorter the measurement time. Furthermore, in a case where the detectability of biometric information is not so high, the measurement time can be increased to achieve measurement of biometric information with high accuracy.

The determination selection unit 113 determines the detectability of the biometric information on the basis of the size of the region range of each of the plurality of part images of the subject.

This makes it possible to determine the detectability of biometric information on the basis of the criterion that the larger the measurement region, the more stable the measurement region is.

The biometric information measurement unit 114 detects the pulse of the subject from each of the plurality of part images of the subject.

The determination selection unit 113 determines the detectability of biometric information on the basis of the pulse detected by the biometric information measurement unit 114.

This makes it possible to determine the detectability of biometric information on the basis of the reference being the pulse.

The biometric information measurement unit 114 calculates a pulse measurement rate on the basis of the detected pulse. The determination selection unit 113 determines the detectability of biometric information on the basis of the pulse measurement rate calculated by the biometric information measurement unit 114.

This makes it possible to determine the detectability of biometric information on the basis of the criterion that the higher the pulse measurement rate, the more stable the measurement region is.

The determination selection unit 113 performs selection every time the image including the subject captured by the imaging unit 16 is updated.

This makes it possible to measure the biometric information with higher accuracy even when the image is updated and the detectability of the biometric information is changed.

The image processing apparatus 1 further includes the light emitting unit 17, and the determination selection unit 113 controls the light emitting unit 17 so that the detectability of the biometric information is enhanced in determination of the detectability of the biometric information of the part image of the subject.

This makes it possible to enhance the detectability of biometric information, enabling measurement of biometric information with higher accuracy.

The image processing apparatus 1 further includes the notification unit 115.

The notification unit 115 makes notification of the part selected by the determination selection unit 113.

This enables the user being the subject to grasp which part is currently selected and to adjust the position or the like of the face so that the selected part is appropriately imaged.

The notification unit 115 makes notification of the biometric information obtained by the biometric information measurement unit 114 in accordance with the region range of the part image selected by the determination selection unit 113.

This makes it possible to automatically arrange and display waveform data, necessary texts or image information for making notification of biometric information in a region not overlapping with the position on which the user's face as the subject is reflected (that is, in the region not overlapping with the user's face). Alternatively, the information can be displayed to be superimposed at a position where the user's face is reflected.

The notification unit 115 makes notification of guidance to a predetermined image captured position in accordance with the image captured position of the subject specified on the basis of the plurality of part images of the subject detected by the image analysis unit 112.

This makes it possible to make notification of the guidance (navigation) to enable appropriate detection of the measurement region. For example, it is possible to use an arrow or a balloon to display the guidance information so that the position and orientation of the user's face captured by the imaging unit 16 are appropriate position and orientation.

The determination selection unit 113 selects a predetermined part image for each of a plurality of parts designated for each of the subjects.

This makes it possible to ensure measurement of biometric information with higher accuracy even when the measurement region having high detectability of biometric information differs for each of the individual users.

In a case where there is a plurality of part images having detectability of biometric information at a predetermined standard or more, the determination selection unit 113 selects any of the part images, and makes selection concerning acquisition of the biometric information of the subject on the basis of the detectability in the selected part image.

This makes it possible to limit the measurement region for detecting biometric information, enabling reduction of the processing of detecting biometric information.

In a case where there is a plurality of part images having detectability of biometric information at a predetermined standard or more, the determination selection unit 113 joins the plurality of part images, and makes selection concerning acquisition of the biometric information of the subject on the basis of the detectability in the part images joined together.

This makes it possible to perform measurement of biometric information with higher accuracy directed to a wider measurement region.

The determination selection unit 113 makes a selection regarding acquisition of the biometric information of the subject on the basis of the detectability in the part image having the highest detectability of biometric information.

This makes it possible to perform measurement of biometric information with higher accuracy directed to a highest leveled measurement region.

[Modifications]

The present invention is not limited to the above-described embodiments, but includes modifications, improvements, or the like within the scope of achieving the object of the present invention.

<Modification in Selection of Biometric Information>

For example, the first biometric information measurement processing in the above-described embodiment may be partially modified. For example, as described above with reference to FIG. 6, in the first biometric information measurement processing, the determination selection unit 113 performs leveling on each of the detection regions detected (corresponding to the processing in step S15) so as to measure the biometric information of the highly leveled measurement region (corresponding to the processing of step S17).

A modification of this would be performed such that the biometric information measurement unit 114 first obtains and measures biometric information (corresponding to the processing of step S17), and then, the determination selection unit 113 performs leveling on each of the detection regions detected (corresponding to the processing of step S15) so as to select a highly leveled measurement region (corresponding to the processing of step S16) to obtain the biometric information of the selected measurement region. The first biometric information measurement processing in this modification will be described below with reference to FIG. 9.

[First Biometric Information Measurement Processing in Modification]

FIG. 9 is a flowchart for explaining a flow of the first biometric information measurement processing executed by the image processing apparatus 1.

In step S61, the setting control unit 111 performs initial setting similarly to step S11.

In step S62, the image analysis unit 112 performs face tracking to detect a measurement region, similarly to step S12.

In step S63, the image analysis unit 112 determines whether the measurement region has been successfully detected. In a case where the measurement region has been successfully detected, it is determined Yes in step S63, and the processing proceeds to step S64. In contrast, in a case where the measurement region has not been successfully detected because the orientation of the user's face is not appropriate, etc., the determination is No in step S63, and the processing returns to step S62.

In step S64, similarly to step S14, the determination selection unit 113 controls the light emitting unit 17 to adjust the illuminance and the color components so as to facilitate measurement of the biometric information.

In step S65, the biometric information measurement unit 114 measures biometric information from all the measurement regions detected in step S62. As described above, this measurement is performed on the basis of the image of the measurement region, and thus, is user noncontact measurement.

In step S66, the determination selection unit 113 performs leveling on each of all measurement regions detected in step S62. Similarly to step S15 described above, the leveling method is performed in accordance with the size of each of the measurement regions and the pulse wave detection rate of each of the measurement regions.

In step S67, the determination selection unit 113 determines whether a highly leveled measurement region (that is, a measurement region with a level at a predetermined level or more) has been detected in the leveling performed in step S66. In a case where a highly leveled measurement region has been detected, it is determined Yes in step S67, and the processing proceeds to step S68. In contrast, in a case where a highly leveled measurement region has not been detected, it is determined No in step S67, and the processing returns to step S64.

In step S68, the determination selection unit 113 selects biometric information measured from the highly leveled measurement region in the leveling performed in step S66 from among the biometric information measured from each of all the measurement regions in step S66.

In step S69, the notification unit 115 makes notification of the biometric information selected in step S68 by using a method of displaying the information on the display unit 19, for example.

In step S70, the setting control unit 111 stores the biometric information selected in step S68 in the measurement data storage unit 201 of the storage unit 20, the measurement data storage server or the like included in the server group 3.

While the above describes that step S70 is executed after step S69 for convenience, step S69 may be executed after step S70, or step S69 and step S70 may be executed in parallel.

In step S71, the setting control unit 111 determines whether to finish the first biometric information measurement processing according to the modification. For example, the setting control unit 111 determines whether to finish the first biometric information measurement processing according to the modification on condition that: the biometric information has been measured a predetermined number of times; the processing end operation has been received from the user; or a predetermined time has elapsed from the start of the first biometric information measurement processing according to the modification.

In a case where such a condition for finishing the first biometric information measurement processing according to the modification is not satisfied, it is determined No in step S71, and the processing returns to step S64. In contrast, in a case where the condition for finishing the first biometric information measurement processing according to the modification is satisfied, it is determined Yes in step S71, and the first biometric information measurement processing according to the modification is finished.

Note that in the first biometric information measurement processing according to the modification performed in subsequent times, it is allowable to configure to omit the processing such as acquisition of the application in step S61.

In the first biometric information measurement processing according to the modification described above, biometric information is measured from each of all the measurement regions detected. In addition, biometric information measured from a highly leveled measurement region is selected from biometric information measured from each of all measurement regions. Thereafter, the selected biometric information is given in notification. Here, since the highly leveled measurement region is a measurement region where biometric information is easy to measure, it is possible to select biometric information measured with higher accuracy by using the first biometric information measurement processing according to the modification.

Furthermore, in the first biometric information measurement processing according to the modification, biometric information is always measured for all measurement regions prior to selection. Therefore, it is possible to obtain biometric information of a highly leveled measurement region all the time as compared with a case where measurement is performed from a part of measurement regions.

<Modification Related to Selection of Measurement Region>

In the above embodiment, steps S15, S16, and S17 are executed to determine whether a highly leveled measurement region (that is, a measurement region of a predetermined level or more) has been detected, and perform measurement of the biometric information directed to the highly leveled measurement region in a case where the highly leveled measurement region has been detected. The present invention is not limited to this, and such processing may be modified.

For example, in a case where a plurality of highly leveled measurement regions has been detected, any one measurement region may be selected from the plurality of highly leveled measurement regions. Thereafter, the biometric information may be detected from the selected one measurement region. This makes it possible to limit the measurement region for detecting biometric information, enabling reduction of the processing of detecting biometric information.

Alternatively, in a case where a plurality of highly leveled measurement regions has been detected, the plurality of highly leveled measurement regions may be joined to be handled as one measurement region (that is, beyond the part boundary between the forehead, cheek, chin, and neck). Furthermore, the biometric information may be detected from the single jointed measurement region. This makes it possible to perform measurement of biometric information with higher accuracy directed to a wider measurement region.

Alternatively, it is allowable to determine to which measurement region the highest leveled measurement region belongs instead of determining whether a highly leveled measurement region (that is, a measurement region of a predetermined level or more) has been detected. It is allowable to subsequently detect the biometric information from the measurement region determined to be the highest leveled measurement region. This makes it possible to perform measurement of biometric information with higher accuracy directed to a highest leveled measurement region.

Note that this modification may be applied to steps S66, S67, and S68 described above with reference to FIG. 9. That is, the present modification may be applied to the processing of selecting biometric information measured from a highly leveled measurement region.

<Other Modifications>

There is another conceivable modification. For example, in step S17 or step S46 in the above-described embodiment, measurement of biometric information is performed without consideration of the level of the measurement region as a measurement target. This may be modified so that the measurement method of the biometric information varies in accordance with the level of the measurement region as a measurement target. For example, it is allowable to configure such that the higher the level of the measurement region, the shorter the measurement time.

More specifically, there may be a case of performing leveling in three stages, for example, high, medium, and low. In this case, the measurement time is set shorter than a prescribed value for high level (region: large/pulse wave detection rate: high), the measurement time is set to a prescribed value (default) for middle level (region: prescribed value/pulse wave detection rate: prescribed value), and the measurement time is set longer than a prescribed value for low level (region: small/pulse wave detection rate: low).

With this configuration, it is possible to measure the biometric information with high accuracy with a short measurement time in a case where the measurement region is highly leveled (that is, in a case where the availability of biometric information is high).

In addition, even in a case where the level of the measurement region is not so high (that is, when availability of biometric information is not so high), biometric information can be measured with high accuracy by increasing the measurement time. That is, even in a case where only a measurement region having a level not so high can be detected, it is still possible to measure biometric information with high accuracy.

There is still another modification. For example, in the above-described embodiment, the first biometric information measurement processing assumed that measurement is performed from one measurement region. Alternatively, however, it is allowable to modify this measurement to perform measurement on two distant measurement regions from which pulse delay is known even in the first biometric information measurement processing as well. That is, it is allowable to measure biometric information such as pulse wave velocity and blood pressure fluctuation by the first biometric information measurement processing.

There is still another modification. For example, the above embodiment assumed that measurement is performed from one measurement region or two measurement regions.

Alternatively, however, it is allowable to perform measurement on three or more measurement regions.

There is still another modification. For example, the above-described embodiment assumed that the image processing apparatus 1 cooperates with each of servers included in the server group 3. Alternatively however, the function of each of the servers may be provided to the image processing apparatus 1 to cause the image processing apparatus 1 alone to execute all the processing.

Furthermore, in the above-described embodiment, while the image processing apparatus 1 to which the present invention is applied is described as an example of an electronic device incorporated in a portable free-standing mirror, the invention is not particularly limited to this example.

For example, the present invention is applicable to electronic equipment incorporated in a large mirror such as a full-length mirror, electronic equipment incorporated in a stationary washbasin, and mirror-shaped electronic equipment installed in a bathroom.

The series of processes described above can be executed by hardware or software.

In other words, the functional configuration of FIG. 5 is merely an example and is not particularly limited. That is, it is sufficient as long as the image processing apparatus 1 includes functions capable of executing the above-described series of processing as a whole, and the type of functional blocks to be used to implement these functions is not particularly limited to the example in FIG. 5.

In addition, one functional block may be constituted by a single piece of hardware, a single piece of software, or a combination thereof.

The functional configuration in the present embodiment is implemented by a processor that executes arithmetic processing. The processor applicable in the present embodiment includes one constituted with a variety of single processing device, such as a single processor, a multiprocessor, and a multi-core processor, as well as a combination of the variety of processing devices with processing circuits such as an application specific integrated circuit (ASIC) and a field-programmable gate array (FPGA).

In a case where a series of processing is executed in software, a program constituting the software is installed from a network or a recording medium to a computer or the like.

The computer may be a computer incorporated in dedicated hardware. The computer may also be a computer capable of executing various functions by installing various programs, for example, a general-purpose personal computer.

The recording medium containing such a program is not merely constituted by the removable medium 100 of FIG. 2 distributed separately from the apparatus main body for providing a program to the user but also a recording medium, etc. supplied to the user in a state of being incorporated into the apparatus. The removable medium 100 is configured by, for example, a magnetic disk (including a floppy disk), an optical disk, a magneto-optical disk, or the like. The optical disk is configured by, for example, a compact disk-read only memory (CD-ROM), a digital versatile disk (DVD), a Blu-ray (registered trademark) disc, or the like. The magneto-optical disk is constituted with Mini-Disk (MD) or the like. Furthermore, the recording medium supplied to the user in a state of being preliminarily incorporated in the apparatus main body is constituted by, for example, the ROM 12 in FIG. 4 recording the program, the hard disk included in the storage unit 20 in FIGS. 4 and 5, or others.

In the present specification, steps describing programs to be recorded on a recording medium are not limited to processing that is performed in time series according to the order of steps, but also include processing to be executed in parallel or individually, not necessarily processed in time series.

Furthermore, in this specification, the term of the system shall mean an entire apparatus including a plurality of apparatuses, a plurality of units, or the like.

Several embodiments of the present invention have been described above, but these embodiments are merely examples and do not limit the technical scope of the present invention. The present invention can adopt various other embodiments, and various modifications such as omission and substitution can be made without departing from the scope and spirit of the present invention. These embodiments and modifications thereof are included in the scope and spirit of the invention described in this specification or the like and are included in the invention described in the claims and the equivalent scope thereof.

What is claimed is:

1. An image processing apparatus comprising a processor, wherein the processor:
    detects a plurality of part images of a subject from an image including the subject captured by an imaging unit,
    determines detectability of biometric information for each of at least two of the plurality of detected part images of the subject based on a detected pulse of the subject from each of the plurality of part images of the subject, and performs selection, from a plurality of parts of the subject, of a part from which the biometric information is to be obtained, based on the determined detectability of the biometric information.

2. The image processing apparatus according to claim 1, wherein the processor:
    selects a predetermined part image from the plurality of part images of the subject based on the determined detectability of the biometric information, and
    obtains the biometric information of the subject from the selected predetermined part image.

3. The image processing apparatus according to claim 1, wherein the processor:
    obtains biometric information for each of the plurality of detected part images of the subject, and
    selects the biometric information from the obtained plurality of pieces of biometric information based on the determined detectability of the biometric information.

4. The image processing apparatus according to claim 2, wherein the processor sets an acquisition method of the biometric information to vary in accordance with the detectability of the biometric information for the selected predetermined part image.

5. The image processing apparatus according to claim 1, wherein the processor determines the detectability of the biometric information based further on a size of a region range of each of the plurality of part images of the subject.

6. The image processing apparatus according to claim 1, wherein the processor:
    calculates a pulse measurement rate based on the detected pulse, and
    determines detectability of the biometric information based on the calculated pulse measurement rate.

7. The image processing apparatus according to claim 1, wherein the processor performs the selection every time the captured image including the subject is updated.

8. The image processing apparatus according to claim 1, further comprising a light emitting unit,
wherein, in a case of determining the detectability of the biometric information for said each of at least two of the plurality of part images of the subject, the processor controls light emission of the light emitting unit so as to increase the detectability of the biometric information.

9. The image processing apparatus according to claim 2, wherein the processor makes notification of a part of the subject corresponding to the selected predetermined part image.

10. The image processing apparatus according to claim 2, wherein the processor makes notification of the obtained biometric information in accordance with a region range of the selected predetermined part image.

11. The image processing apparatus according to claim 1, wherein the processor makes notification of guidance to a predetermined image captured position in accordance with an image captured position of the subject specified based on the detected plurality of part images of the subject.

12. The image processing apparatus according to claim 2, wherein the processor selects the predetermined part image for each of a plurality of parts designated for each of a plurality of subjects.

13. The image processing apparatus according to claim 1, wherein, in a case where there is a plurality of part images having detectability of biometric information at a predetermined standard or more, the processor selects any of the part images, and performs selection of the part from which the biometric information of the subject is to be obtained based on the detectability in the selected part image.

14. The image processing apparatus according to claim 1, wherein, in a case where there is a plurality of part images having detectability of biometric information at a predetermined standard or more, the processor joins the plurality of part images, and performs selection of the part from which the biometric information of the subject is to be obtained based on the detectability in the part images joined together.

15. The image processing apparatus according to claim 1, wherein the processor performs selection of the part from which the biometric information of the subject is to be obtained based on the detectability in the part image having a highest detectability of the biometric information among the at least two part images.

16. An image processing method executed by an image processing apparatus including a processor, the method comprising:
    detecting a plurality of part images of a subject from an image including the captured subject;
    determining detectability of biometric information for each of at least two of the plurality of detected part images of the subject based on a detected pulse of the subject from each of the plurality of part images of the subject; and
    performing selection, from a plurality of parts of the subject, of a part from which the biometric information is to be obtained, based on the determined detectability of the biometric information.

17. A non-transitory computer-readable recording medium on which a computer readable program to be executed by an image processing apparatus including a processor is recorded, the program being executable by the processor of the image processing apparatus to implement:
    a part detecting function of detecting a plurality of part images of a subject from an image including the captured subject;
    a determination function of determining detectability of biometric information for each of at least two of the plurality of detected part images of the subject based on a detected pulse of the subject from each of the plurality of part images of the subject; and
    a selection function of performing selection, from a plurality of parts of the subject, of a part from which the biometric information is to be obtained, based on the determined detectability of the biometric information.

* * * * *